United States Patent [19]
Yoshino et al.

[11] Patent Number: 5,568,599
[45] Date of Patent: Oct. 22, 1996

[54] ELECTRONIC MONTAGE CREATION DEVICE

[75] Inventors: Hiroyuki Yoshino, Higashiyamato; Takashi Kojo, Ome, both of Japan

[73] Assignee: Casio Computer Co., Ltd., Tokyo, Japan

[21] Appl. No.: 587,829

[22] Filed: Jan. 11, 1996

Related U.S. Application Data

[63] Continuation of Ser. No. 212,114, Mar. 11, 1994.

[30] Foreign Application Priority Data

Mar. 18, 1993 [JP] Japan ................................. 5-085519

[51] Int. Cl.⁶ ................................................. G06F 15/72
[52] U.S. Cl. ................................................... 395/135
[58] Field of Search ................................. 395/133, 135, 395/155, 161; 434/155; 382/46, 48

[56] References Cited

U.S. PATENT DOCUMENTS

| | | |
|---|---|---|
| 4,791,581 | 12/1988 | Ohba . |
| 4,885,702 | 12/1989 | Ohba . |
| 4,913,539 | 4/1990 | Lewis . |
| 5,057,019 | 10/1991 | Harvey . |
| 5,111,409 | 5/1992 | Gasper et al. ............... 395/152 |
| 5,247,610 | 9/1993 | Oshima et al. . |
| 5,272,769 | 12/1993 | Strnatka et al. . |
| 5,313,408 | 5/1994 | Goto . |
| 5,375,195 | 12/1994 | Johnston . |
| 5,487,140 | 1/1996 | Toya ................................. 395/135 |

FOREIGN PATENT DOCUMENTS

| | | |
|---|---|---|
| 1546072 | 5/1979 | European Pat. Off. . |
| 0225729 | 6/1987 | European Pat. Off. . |
| 0275124 | 7/1988 | European Pat. Off. . |
| 0584699A1 | 3/1994 | European Pat. Off. . |
| 3-129572 | 6/1991 | Japan . |

OTHER PUBLICATIONS

Systems and Computers in Japan, vol. 19, No. 9, Sep. 1988, U.S. pp. 1–9, Noguchi et al, "A Method of Generating Facial Expressions using a Database–Driven Animation System".

IBM Nachrichten, vol. 34, No. 272, Aug. 1984, West Germany, pp. 41–44, ZIMA, "Am Bildschirm zu Konstruieren: Physiognomien".

*Primary Examiner*—Phu K. Nguyen
*Attorney, Agent, or Firm*—Frishauf, Holtz, Goodman, Langer & Chick

[57] ABSTRACT

A montage image creating apparatus which selectively designates one of the patterns of each of a plurality of parts which constitutes a human face, and which combines the respective designated part patterns to form a montage image of the face of a person. The apparatus selectively designates a pattern of at least one of a plurality of parts on the basis of a personality character of the person, which personality character is designated by a character designating unit.

23 Claims, 22 Drawing Sheets

FIG.4
41
| PART \ NO. | 1 | 2 | 3 |
|---|---|---|---|
| OUTLINE | PRUDENT  | OPTIMISTIC  | PESSIMISTIC 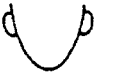 |
| HAIR STYLE | PUNCTUAL  | CLEAN  | SLOVEN  |
| EYE-BROWS | AGGRESSIVE  | SPECULATIVE  | PASSIVE  |
| EYES | SERIOUS  | FRIVOLOUS  | CAPRICIOUS  |

FIG.5
41
| PART \ NO. | 1 | 2 | 3 | |
|---|---|---|---|---|
| OUTLINE | PRUDENT  | OPTIMISTIC  | PESSIMISTIC  | |
| HAIR STYLE | PUNCTUAL  | CLEAN  | SLOVEN  | |
| EYE-BROWS | AGGRESSIVE  | SPECULATIVE  | PASSIVE  | |
| EYES | SERIOUS  | FRIVOLOUS  | CAPRICIOUS  | |
| | | | | |

FIG.6

| PART \ NO. | 1 | | 2 | | 3 | |
|---|---|---|---|---|---|---|
| OPTIMISTIC | OUTLINE<br>HAIR STYLE<br>EYE-BROWS<br>⋮ | 1<br>10<br>15<br>⋮ | OUTLINE<br>HAIR STYLE<br>EYE-BROWS<br>⋮ | 2<br>8<br>30<br>⋮ | ⋮<br>⋮<br>⋮<br>⋮ | ⋮<br>⋮<br>⋮<br>⋮ |
| PESSIMISTIC | OUTLINE<br>HAIR STYLE<br>EYE-BROWS<br>⋮ | 10<br>2<br>3<br>⋮ | ⋮<br>⋮<br>⋮<br>⋮ | ⋮<br>⋮<br>⋮<br>⋮ | ⋮<br>⋮<br>⋮<br>⋮ | ⋮<br>⋮<br>⋮<br>⋮ |
| AGGRESSIVE | OUTLINE<br>HAIR STYLE<br>EYE-BROWS<br>⋮ | 15<br>6<br>7<br>⋮ | ⋮<br>⋮<br>⋮<br>⋮ | ⋮<br>⋮<br>⋮<br>⋮ | ⋮<br>⋮<br>⋮<br>⋮ | ⋮<br>⋮<br>⋮<br>⋮ |

FIG.7

| PART \ NO. | 1 | 2 | 3 | |
|---|---|---|---|---|
| OPTIMISTIC | OUTLINE : <br> HAIR STYLE : <br> EYE-BROWS : <br> ⋮ | OUTLINE : <br> HAIR STYLE : <br> EYE-BROWS : <br> ⋮ | : <br> : <br> : <br> : <br> : | : <br> : <br> : <br> : <br> : |
| PESSIMISTIC | OUTLINE : <br> HAIR STYLE : <br> EYE-BROWS : <br> ⋮ | : <br> : <br> : <br> : <br> : | : <br> : <br> : <br> : <br> : | : <br> : <br> : <br> : <br> : |
| AGGRESSIVE | OUTLINE : <br> HAIR STYLE : <br> EYE-BROWS : <br> ⋮ | : <br> : <br> : <br> : <br> : | : <br> : <br> : <br> : <br> : | : <br> : <br> : <br> : <br> : |
| | | | | |

FIG.8
| CHARACTER \ NO. | 1 | 2 | 3 | |
|---|---|---|---|---|
| OPTIMISTIC |  |  |  | |
| PESSIMISTIC |  |  |  | |
| AGGRESSIVE |  |  |  | |
| | | | | |

FIG.9

| CHARACTER \ NO. | 1 | 2 | 3 | |
|---|---|---|---|---|
| OPTIMISTIC | | | | |
| PESSIMISTIC | | | | |
| AGGRESSIVE | | | | |
| | | | | |

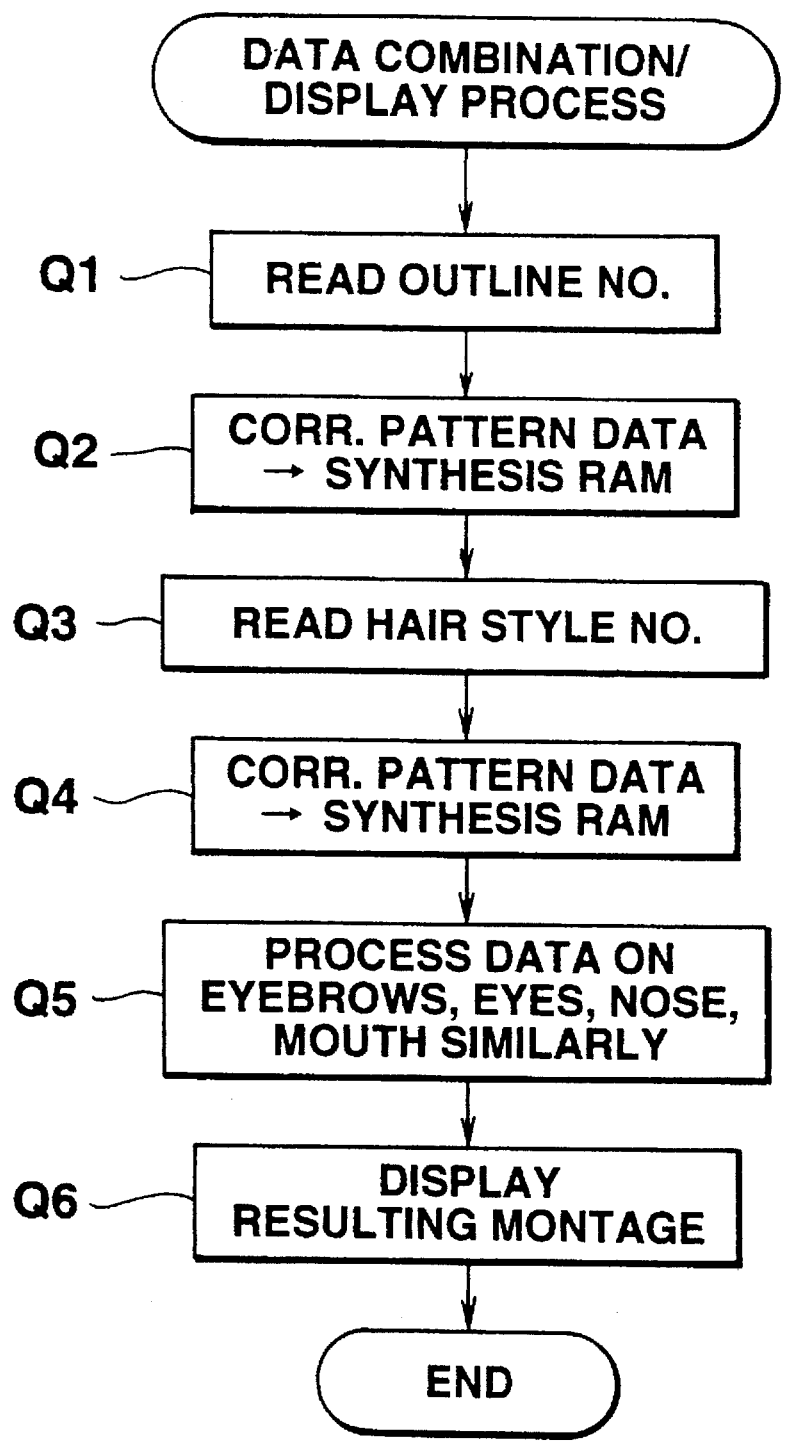

FIG.18(c)  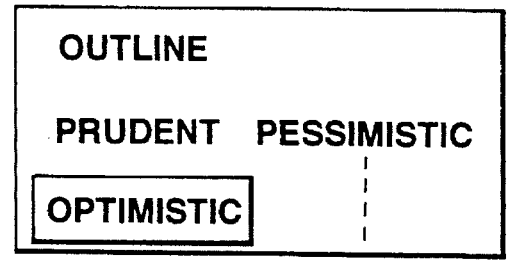

FIG.21

| CHARACTER | | | EACH PART PATTERN NO. OR BASIC FACE NO. |
|---|---|---|---|
| OPTIMISTIC | PUNCTUAL | SERIOUS | |
| 1 | 1 | 1 | 1 |
| 1 | 1 | 2 | 2 |
| 1 | 1 | 3 | 3 |
| 1 | 1 | 4 | 4 |
| ⌇ | ⌇ | ⌇ | ⌇ |
| 5 | 5 | 4 | 1 2 4 |
| 5 | 5 | 5 | 1 2 5 |

ELECTRONIC MONTAGE CREATION DEVICE

This application is a Continuation of application Ser. No. 08/212,114, filed Mar. 11, 1994.

BACKGROUND OF THE INVENTION

The present invention relates to electronic montage creation devices which create the image of a face.

Conventionally, small portable electronic devices have been sold as articles which are typified by electronic notebooks which, for example, stores data on input names, addresses, telephone numbers beforehand and displays such data, as required.

Such device is capable of storing and displaying only data on letters and numerals and cannot sometimes remind user of a person's figure (especially, his face) from displayed data.

It could be conceived to beforehand store data on persons' names, addresses, and telephone numbers along with data on their images obtained from their photographs, using an image scanner, and to display a person's name, address, and telephone number along with his image. Generally, the amount of image data is immense, so that there is the problem that the image data would easily overflow a memory of a small portable electronic device when it is stored as it is in the memory.

Electronic notebooks with a montage display function have been put to practical use which combine a plurality of pattern images prepared beforehand to display the resulting montage to thereby handle a greatly reduced amount of data in order to cope with the above problem.

Those notebooks prepare a plurality of pattern images of each of the arts of a person's face such as an outline, a hair style, a front hair, eyebrows, eyes, a nose and a mouth, selects a pattern image having an appropriate form for each part by means of a number, combines those selected part patterns into a montage image, and displays same.

For example, even when the owner of the electronic notebook cannot reminded of a person's face from data on his name, address and telephone number alone, he can instruct the notebook to display a montage image which gets a clue to reminding of the face of the recorded person.

Thus, the image of a person's face can be displayed without increasing the capacity of the data memory.

However, as described above, such conventional montage display electronic notebook which is a montage display prepares a plurality of pattern images of each of the parts of a face which are an outline, a hair style, a front hair, eyebrows, eyes, a nose and a mouth, and combines selected pattern images into a person's face image. Thus, the notebook has the following problems.

In the creation of a montage, the user selects by visual comparison pattern images closest to the respective parts of a person's face whose montage is to be created from prepared pattern images of each of the outlines, hair styles, etc. In this case, the number of pattern images combined is immense, so that operation is troublesome and substantial skill is required to create a montage similar to the face of a target person.

Thus, although the electronic notebook has the function of creating a montage, there are only a few users who are able to use that function effectively. In some cases, no montage functions were used.

In order to simplify the creation of a montage as much as possible, the present inventors filed an application for a patent on an electronic montage creation device which prepared for several basic face patterns beforehand, selected the most appropriate ones from among those basic face patterns, and changed the respective part pattern images of the selected basic face pattern to finish a target montage image (U.S. Ser. No. 08/062,994, now U.S. Pat. No. 5,537,662 issued on Jul. 16, 1996).

This device, however, must also select by visual comparison pattern images of the parts of a face closest to a person's face to be created from among a plurality of prepared pattern images of each of the respective parts of the person's face. In order to create a montage similar to the face of the target person, some skill is required.

SUMMARY OF THE INVENTION

It is an object of the present invention to provide an electronic montage creation device capable of creating a target image easily by a simple operation.

In order to achieve the above object, according to the present invention, there is provided an electronic montage creation device including:

pattern storage means for storing a plurality of patterns of each of a plurality of parts which constitute a face;

character designating means for designating a character;

pattern selectively designating means for selectively designating a pattern of each of the plurality of parts on the basis of a character designated by the character designating means; and means for combining the respective patterns of the parts designated by the pattern selectively designating means into a montage image and displaying the montage image.

According to this structure, only selection and designation of a character leads to selective designation of the respective patterns of the parts which constitute a face to thereby create a montage image automatically on the basis of the designated patterns. Thus, this structure is very easy to operate to achieve the object.

BRIEF DESCRIPTION OF THE DRAWINGS

FIG. 4 shows a stored state of data on the patterns of male parts in a part pattern ROM of FIG. 2;

FIG. 5 shows a stored state of data on the patterns of female parts in the part pattern ROM of FIG. 2;

FIG. 6 shows a stored state of data on the patterns of the parts of a male basic face in the part pattern ROM of FIG. 2;

FIG. 7 shows a stored state of data on the patterns of the parts of a female basic face in the part pattern ROM of FIG. 2;

FIG. 8 shows a montage image created with data on the patterns of the parts of the male basic face of FIG. 6;

FIG. 9 shows a montage image created with data on the patterns of the parts of the female basic face of FIG. 7;

FIG. 17 is a flowchart indicative of the details of data combination/display process of FIGS. 13, 14 and 16;

FIGS. 18(a)–18(e) illustrate an individual part selecting mode subprocess of the montage creation process of FIGS. 12 and 13;

FIG. 21 shows a stored state of a storage which stores the relationship in correspondence between the level of person's character and a respective part pattern or basic face in the montage creation device of the second embodiment.

DESCRIPTION OF THE PREFERRED EMBODIMENTS (1) First Embodiment:

A first embodiment of an inventive electronic montage creation device will be described below in conjunction with FIGS. 1–17.

Figure 1:
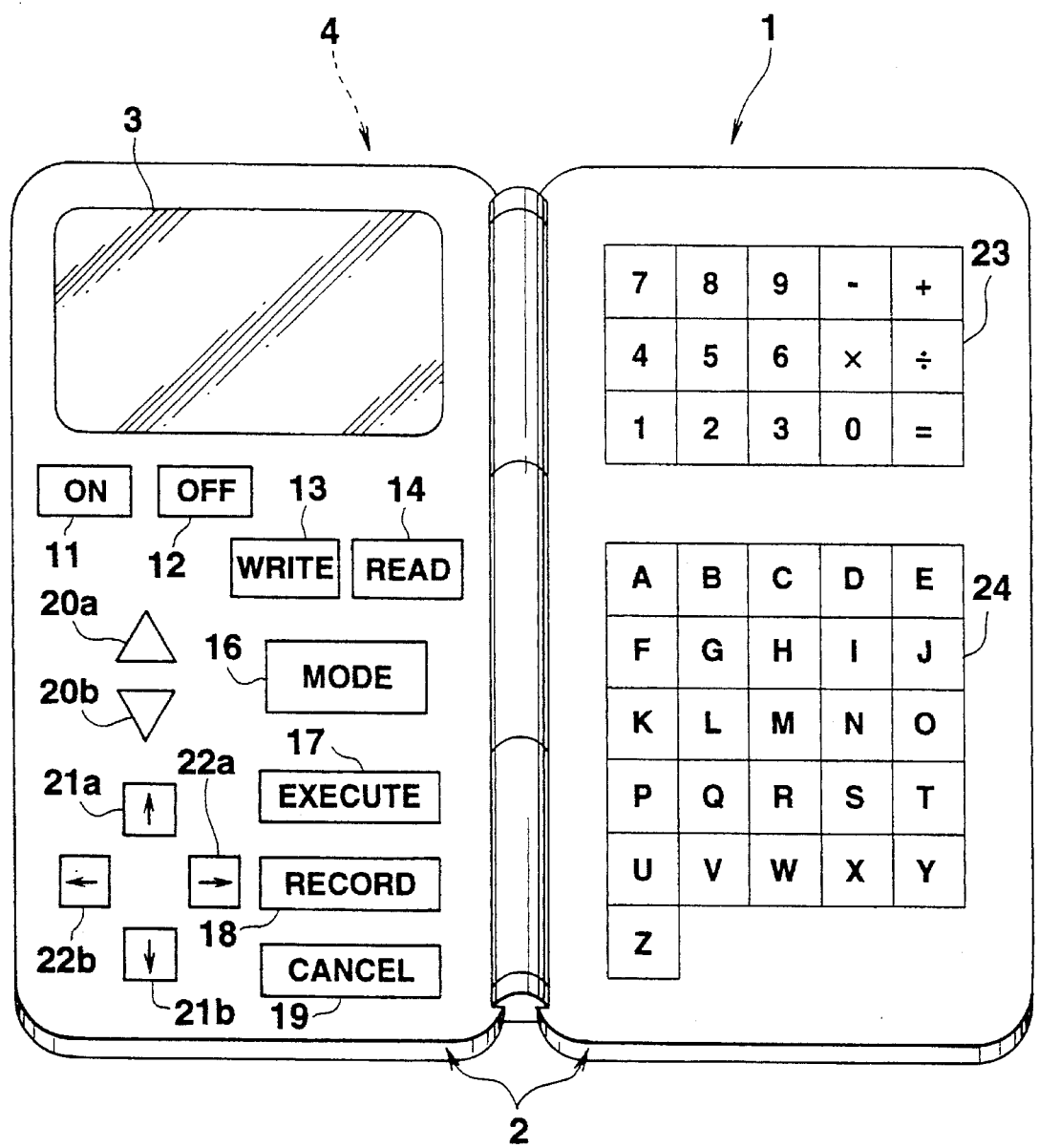
FIG. 1 shows the appearance of an electronic notebook to which a montage creation device of a first embodiment of the present invention is applied.

FIG. 1 shows the appearance of an electronic notebook to which the electronic montage creation device of the first embodiment is applied.

In FIG. 1, the electronic notebook 1 is composed of an input unit 2, display unit 2 and internal unit 4.

The input unit 2 is provided with a power supply on switch 11, power supply off switch 12, write key 13, read key 14, mode selection key 16, execute key 17, record key 18, cancel key 19, upper selection key 20a, lower selection key 20b, upward arrow key 21a, downward arrow key 21b, rightward arrow key 22a, leftward arrow key 22b, ten-key unit 23, and alphabetical key unit 24.

The power supply on key 11 is used to turn on a power supply (not shown) when the notebook 1 is used while the power supply off key 12 is used to turn off the power supply.

The write key 13 is used to start writing individual's data on his name, address, telephone number, etc., into a memory (not shown) while the read key 13 is used to start reading and displaying stored individual's data from the memory.

The mode selection key 16 is used in the montage creation mode to select one of an "individual part selection mode" in which all the patterns of the parts as the components of a person's face which are the "outline", "hair style", eyebrows", "eyes", nose", and "mouth" are selected one for each part and combined into a montage image and a "basic face changing mode" in which a montage image of a basic face is first displayed and the respective patterns of the parts of the basic face are changed to form another montage image.

The execute key 17 is used to fix a selected one of various items displayed on the display 3 in the montage creation process.

The record key 18 is used to temporarily or semi-permanently fix a created montage in the montage creation process.

The cancel key 19 is used to cancel a montage image created by selection of the respective patterns of the parts in the individual part selection mode of the montage creation process.

The upper and lower selection keys 20a and 20b are used to selectively designate a stored plurality of individual's data items and display the designated individual's data items on the display 3 and to select one of the plurality of basic faces set in correspondence to persons' characters in the basic face changing mode of the montage creation process.

The upward, downward arrow keys 21a, 21b, and rightward and leftward arrow keys 22a, 22b are used to select one of various items displayed on the display 3 in the montage creation process. The upward and downward arrow keys 21a and 21b are used to selectively designate parts (outline, hair style, eyebrows, eyes, nose and mouth) the pattern images of which are desired to be changed. The rightward and leftward arrow keys 22a and 22b are used to change the respective pattern images of the parts of a montage image.

The ten-key unit 23 is composed of numerical keys "0"–"9" and arithmetic operation keys "–", "+", "×", "+". "=" and used to input data shown on the respective key tops.

The alphabetical key unit 24 is composed of alphabetical keys "A"–"Z" and used to input data shown on the respective key tops as is the ten-key unit 23.

Figure 2:
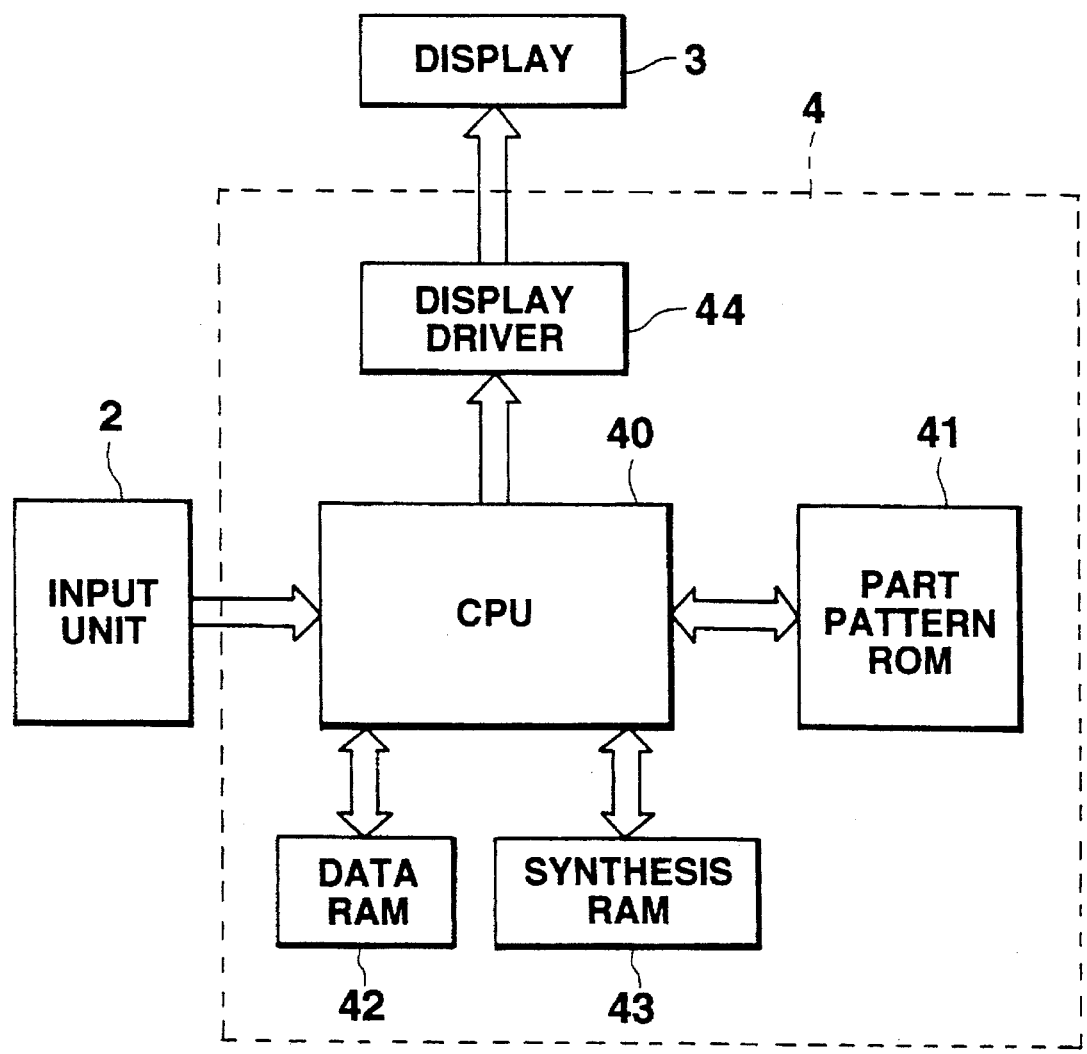
FIG. 2 is a block diagram indicative of the circuit configuration of the electronic notebook of FIG. 1.

FIG. 2 is a block diagram indicative of the internal structure of the electronic notebook of FIG. 1. The display 3 is composed of an LCD (Liquid Crystal Display) and displays letter and numeral data output from the internal unit 4 and displays a desired image on the basis of an image signal generated by the internal unit 4. More specifically, it displays a person's name, address, telephone number and montage image. As shown in FIG. 2, the internal unit 4 is composed of a CPU (Central Processing Unit) 40, part pattern ROM (Read Only Memory) 41, data RAM (Random Access Memory) 42, synthesis RAM 43, and display driver 44.

The CPU 40 outputs various control signals to control the whole electronic notebook 1.

Figure 3:
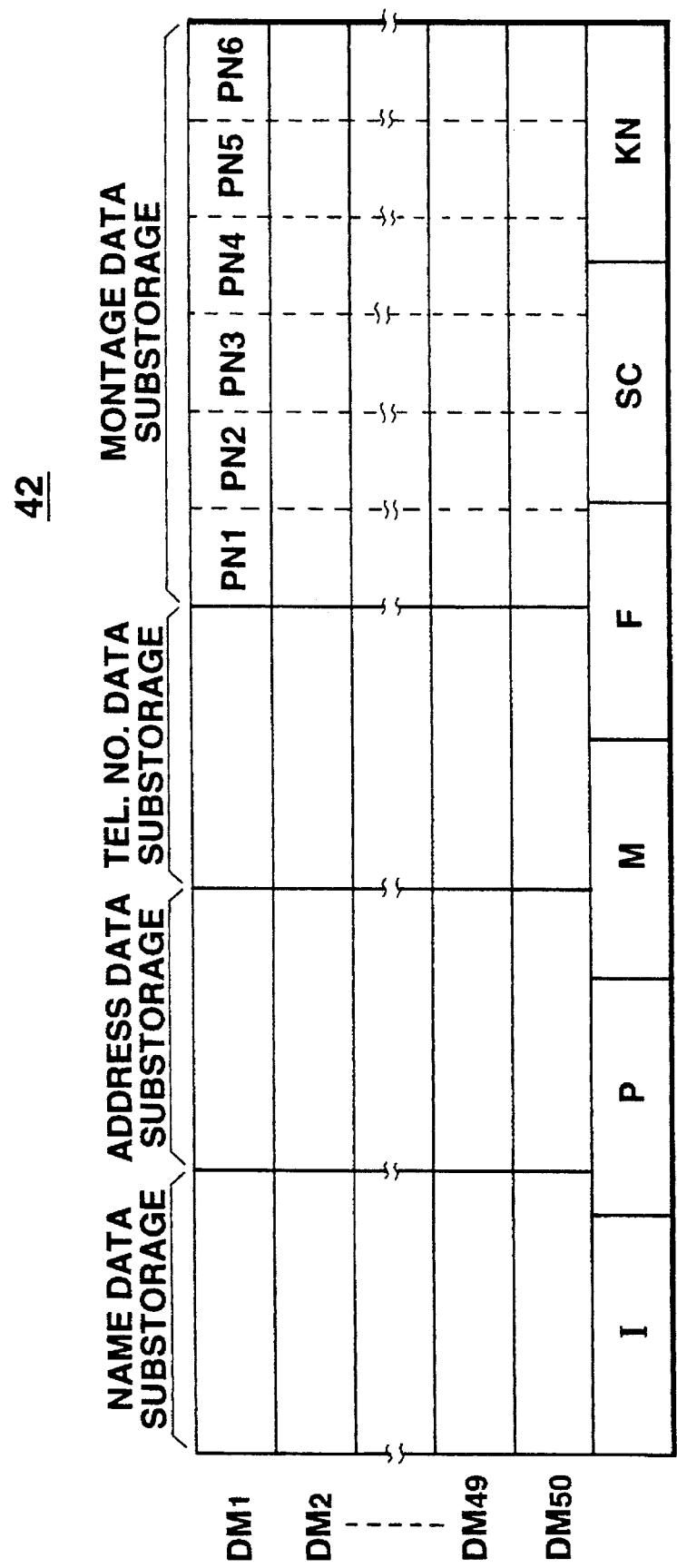
FIG. 3 shows the structure of a data RAM of FIG. 2.

FIG. 3 shows the structure of the data RAM 42 which is provided with 50 individual's data storages $DM_1$-$DM_{50}$, registers I and P, mode register M, sex discrimination register F, and registers SC and KN.

The 50 individual's data storages $DM_1$-$DM_{50}$ each have a capacity to store individual's data; that is, data on 50 individuals in all. Each data storage is composed of name, address, telephone number and montage data substorages.

The montage data substorage stores data on a number indicative of a selected pattern image of each of the parts "outline", "hair style", "eyebrows", "eyes", "nose", and "mouth". It is composed of a substorage PN1 which stores data on a number indicative of a selected pattern image of the part "outline", a substorage PN2 which stores data on a number indicative of a selected pattern image of the part "hair style", a substorage PN3 which stores data on a number indicative of a selected pattern image of the part "eyebrows", a substorage PN4 which stores data on a number indicative of a selected pattern image of the part "eyes", a substorage PN5 which stores data on a number indicative of a selected pattern image of the part "nose" and a substorage PN6 which stores data on a number indicative of a selected pattern image of the part "mouth".

The register I is used to selectively designate the 50 individual's data storages $DM_1$-$DM_{50}$ when data on an individual is written into the designated storage.

The register P is used to selectively designate the 50 individual's data storages $DM_1$-$DM_{50}$ when data on an individual is read from the designated storage.

The mode register M is used to store a mode of selection.

The montage display device of the first embodiment operates in an "individual part selection mode" where all the pattern images of the parts "outline", "hair style", "eyebrows", "eyes", "nose" and "mouth" of a face are selected one for each part, and combined to into a montage image and a "basic face modifying mode" where the montage image of a basic face is first displayed and the respective pattern images of the parts of the basic montage image are changed into another montage.

Numerals "0" and "1" are stored in the "individual part selection mode" and "basic face changing mode", respectively, in the mode register M.

The sex discrimination register F stores data on sex discrimination, that is, "0" and "1", when a male and a female, respectively, are selectively designated.

The register SC stores data on a number indicative of a person's character selectively designated in the basic face changing mode of the montage creation process.

The register KN stores data on a number indicative of a selectively designated one of a plurality of basic faces provided in correspondence to the designated person's character in the basic face changing mode of the montage creation process.

The part pattern ROM 41 stores data on the patterns of male parts along with data on the associated characters, as shown in FIG. 4, and data on the patterns of female parts along with data on the associated characters, as shown in FIG. 5.

More specifically, as shown in FIGS. 4 or 5, a plurality of pattern data items, one indicative of a pattern image of FIGS. 4 or 5, of each of 6 kinds of parts "outline", "hair style", "eyebrows", "eyes", "nose" and "mouth" of a person's face is stored along with a data item on the corresponding character.

For example, for the "outline", pattern data on a "circular outline" image associated correspondingly with a personality character "prudent" is stored at address No. 1. Pattern data on a "rectangular outline" image associated correspondingly with a personality character "optimistic" is stored at address No. 2. Pattern data on an "inverted-triangular outline" image associated correspondingly with a personality character "pessimistic" is stored at address No. 3.

For example, for the "hair style", pattern data on an "arranged hair style" image associated correspondingly with a character "punctual" is stored at address No. 1. Pattern data on a "hair style with a sensation of cleanliness" image associated correspondingly with a character "clean" is stored at address No. 2. Pattern data on an "disordered hair style" image associated correspondingly to a character "sloven" is stored at address No. 3.

As shown in FIGS. 6 and 7, the part pattern ROM 41 stores data on numbers indicative of the respective pattern images of the parts of each of basic faces in correspondence to data on the associated personality characteristics in order to display that basic face corresponding to that character in the "basic face changing mode".

FIG. 6 shows a storage for data for creation of a plurality of male faces. The storage includes data on a plurality of basic face data substorages for each of characters such that a plurality of basic faces is displayed in correspondence to a character with each basic face data substorage storing data on a number indicative of a pattern image of each of the parts "outline", "hair style", "eyebrows", "eyes", "nose", and "mouth". One face montage image is composed of a combination of pattern images designated by data on a set of numbers stored in one basic face data substorage.

Since the plurality of basic face data substorages is provided for each character, a plurality of basic faces can be created for each character. Similarly, FIG. 7 shows a female basic face data storage.

FIGS. 8 and 9 each show montage images created on the basis of data stored in the plurality of basic face data substorages for each of the characters of FIGS. 6 and 7.

The synthesis RAM 43 is composed of a VRAM (Video RAM) which combines pattern data on the respective parts read out from the part pattern ROM 41 on the basis of data on numbers indicative of selected ones of the pattern images of each of the parts stored in the montage data substorage of each of the individual's data storages $DM_1$-$DM_{50}$ of the data RAM 42, and holds the resulting image data.

The synthesis RAM 43 is composed of a memory of X bits (vertical)×Y bits (horizontal) in correspondence to a montage display of X dots (vertical)×Y dots (horizontal) of the display 3. One dot in the display 3 corresponds to one bit in the RAM 43 such that "1", "0" are stored in the synthesis RAM 43 in the same pattern as a montage image.

The display driver 44 converts various displayed data including image data in the synthesis RAM 43 output from the CPU 40 to an image signal displayable on the display 3 and outputs the image signal.

Operation

The operation of the electronic notebook of the first embodiment will now be described with respect to the flowcharts of FIGS. 10–17, FIGS. 18(a)–18(e) and FIGS. 19(a)–19(d).

This electronic notebook has the function of storing the names, addresses, telephone numbers, etc., of many persons, reading and displaying those stored data, as required.

Figure 10:
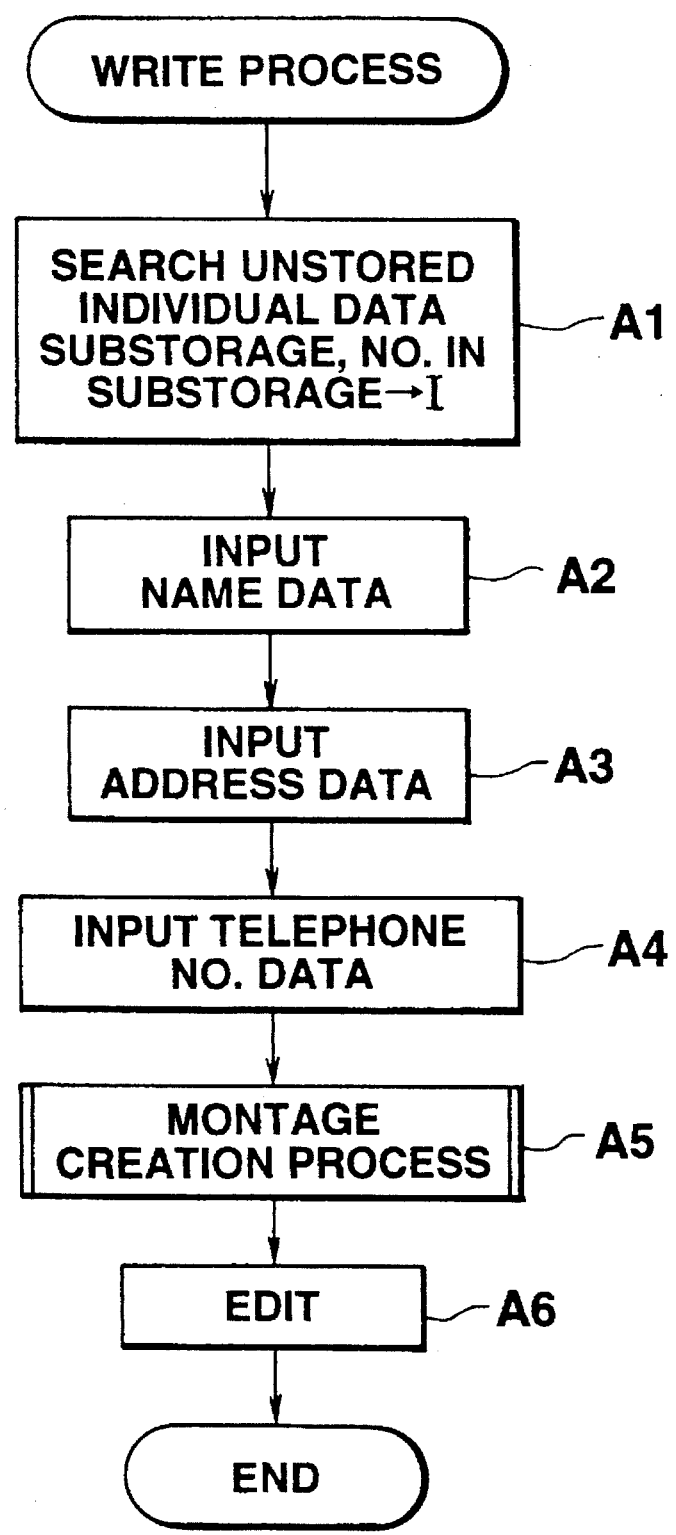
FIG. 10 is a flowchart indicative of the operation of storing individual's data in the electronic circuit of FIG. 2 in a memory.

First, when person's name, address, and telephone number are stored, the write key 13 is operated, which starts a write process of FIG. 10. In this process, that of the 50 individual's data storages $DM_1$-$DM_{50}$ in which no individual's data has been written is sought and a number indicative of that storage is set in the register I at step A1. If individual's data is stored in every one of the 50 storages, any individual's data for one person is erased and required data is then written.

Control then passes to step A2, where name data is input; at step A3 address data is input; and at step A4 telephone number data is input.

In the inputting processes at steps A2–A4, the name, address and telephone number data items are input by means of the ten-key unit 23 and alphabetical key unit 24 and stored in the individual's storage $DM_I$ of the 50 storages $DM_1$-$DM_{50}$ designated by the register I.

After the inputting processes at steps A2–A4, a montage creation process at step A5 is executed to thereby store data on the numbers indicative of the respective patterns images of the parts of the face in the substorages PN1–PN6 of the montage data storage $DM_I$.

After step A5, control passes to step A6, where when a plurality of individual's data items is stored in the 50 storages $DM_1$-$DM_{50}$, edition including a re-storing operation of those individual's data items is made such that those data items are arranged in alphabetical order in terms of name and the write process is then terminated.

Figure 11:
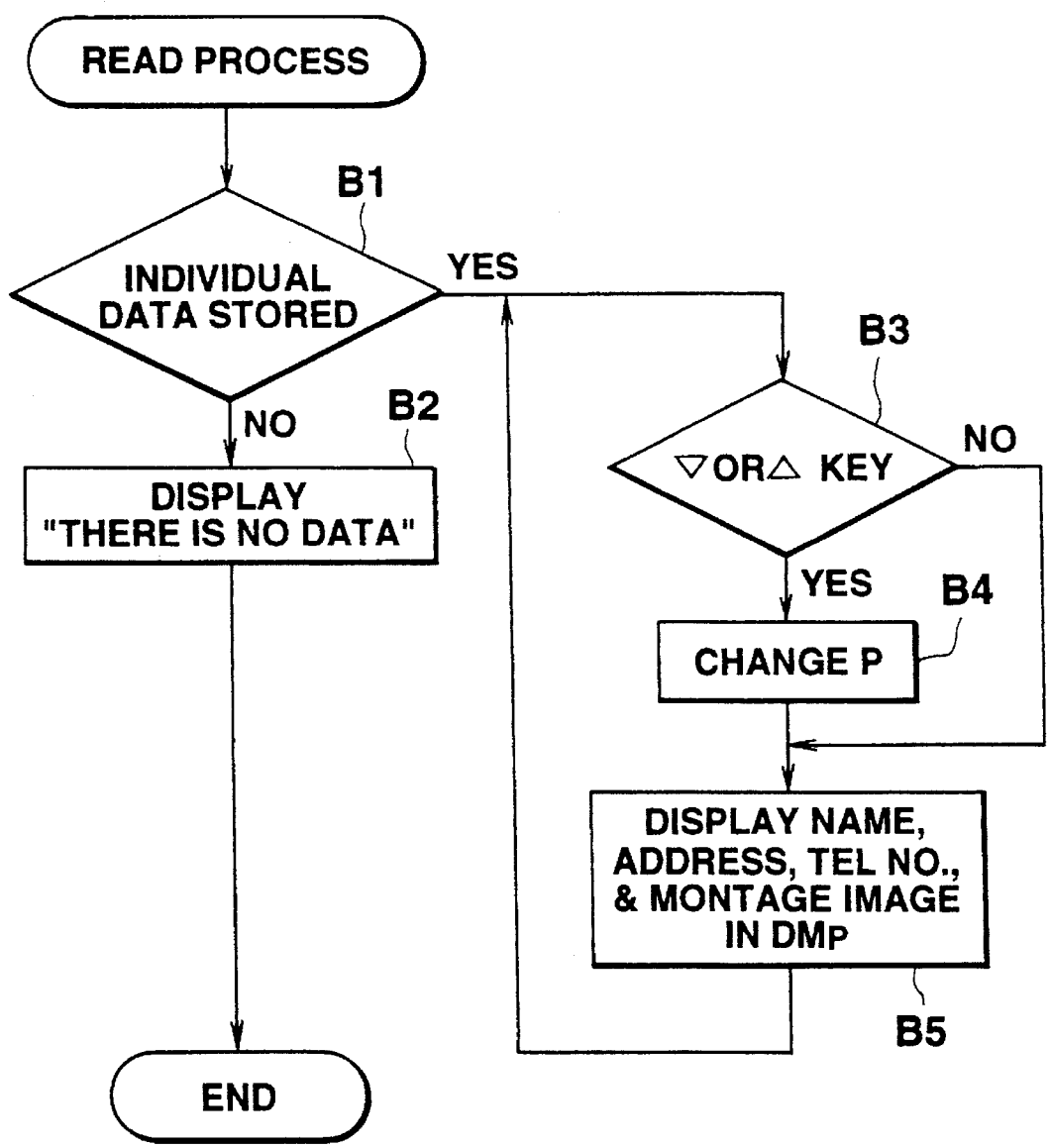
FIG. 11 is a flowchart indicative of the operation of reading individual's data from the memory of the electronic circuit of FIG. 2.
Figure 12:
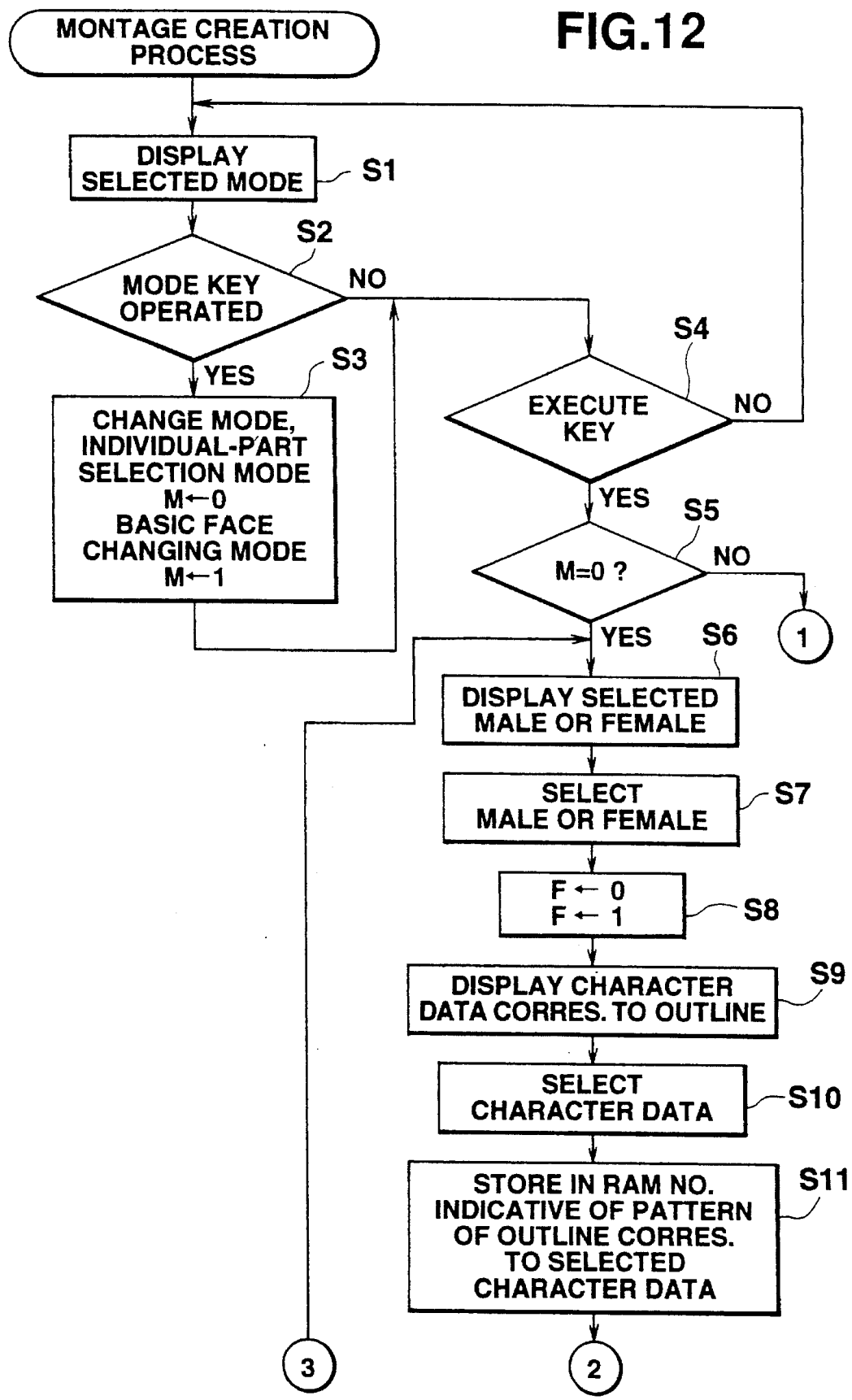
FIG. 12 is a flowchart indicative of the details of the montage creation process of FIG. 10.

When individual's data stored in the storages $DM_1$-$DM_{50}$ is desired to be read and displayed, the user operates the read key 14, which executes the read process of FIG. 11. In this process, it is determined at step B1 whether individual's data is stored in the storages $DM_1$-$DM_{50}$. If not, control passes to step B2, where "there is no data stored in the storages $DM_1$-$DM_{50}$" is displayed and the read process is then terminated.

If the answer is affirmative at step B1, control passes to step B3, where it is determined whether either of the upper and lower selection keys 20a and 20b is operated. If so, the value of the register P to selectively designate one of the storages $DM_1$-$DM_{50}$ is changed to select and designate data on the next or last individual name in alphabetical order.

After step B4, control passes to step B5, where the individual's data (name, address, telephone number) in a storage $DM_P$ of the storages $DM_1$-$DM_{50}$ selectively designated by the register P is displayed. Simultaneously, the respective pattern images of parts of a face are combined to create and display a montage image on the basis of data on the numbers indicative of the respective pattern images of the parts of the face stored in the montage data substorage Mp.

After the display process at step B5, control returns to step B3, where the process steps B3 and subsequent steps are iterated.

FIGS. 12–17 show the montage creation process at step A5 of FIG. 10. First, at step S1 the name of a selected one of the individual part selection mode and the basic face changing mode is displayed. In this case, the mode register is 0 in the default state, so that the individual part selection mode has been selectively designated. Thus, the individual part selection mode is displayed.

Control then passes to step S2, where it is determined whether the mode key 16 has been operated. If so, control passes to step S3, where the mode is changed. That is, when the mode key 16 is operated in the basic face changing mode, the individual part selection mode is newly selected and "0" is stored in the register M. When the mode key 16 is operated in the part selection mode, the basic face mode is newly selected and "1" is stored in the register M.

When it is determined at step S2 that the mode key 16 is not operated, or when the process at step S3 is executed, control passes to step S4, where it is determined whether the execute key 17 has been operated or whether the creation of a montage is executed in the selected and displayed mode.

When the execute key 17 is operated, the displayed mode is fixed as the operative mode.

Control then passes to step S5, where it is determined whether the mode register M is 0. If so, the individual part selection mode process at step S6 and subsequent steps is executed. If not at step S5, that is, if the mode register M is 1, the basic face changing process (FIGS. 15, 16) starts which will be described in detail later.

Figure 18A:
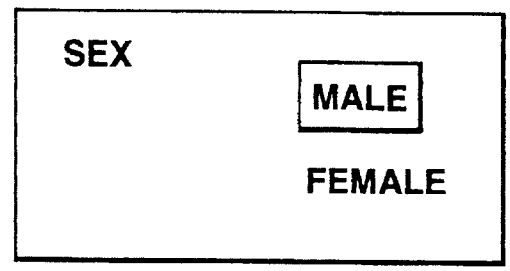

In the individual part selection mode, the selected sex is first displayed at step S6. Control then passes to step S7, where either "male" or "female" is selected. In this case, as shown in FIG. 18(a), "male" is selected in the default state. Thus, if "male" is to be selected, the execute key 17 is only required to be operated. If "female" is to be selected, the lower selection key 20b should be depressed to change the selected state to "female" and then the execute key should be operated.

If "male" is selected as the sex discrimination at step S8, "0" is input to the sex discrimination register F while if "female is selected, "1" is input to the sex discrimination register F.

Control then passes to step S9, where a list of "character" data corresponding to data on the "outline" of the parts of FIGS. 4 or 5 stored in the part pattern ROM 41 is displayed on the basis of the value of the "sex discrimination" register F.

Control then passes to step S10, where a character data selection process is performed. At this step, the upward and downward arrow keys 21a, 21b and rightward and leftward arrow keys 22a and 22b are operated to move a cursor to a target one of the list of "character" data and operate the execute key to select the target "character" data.

Figure 18B:
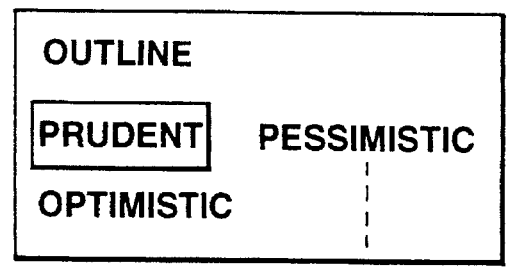

In that case, in the above example, "prudent" is selected in the default state, as shown in FIG. 18(b); the downward arrow key 21b is operated to select "optimistic", as shown in FIG. 18(c); and the execute key 17 is operated to select "optimistic" character data for the "outline" for fixing purposes.

Control then passes to step S11, where data on the number indicative of a pattern image in the part pattern ROM 41 corresponding to the "character" data selected for the "outline" is stored in the substorage PN1 which stores data on a number indicative of the pattern image of the "outline" in the montage data substorage of the individual's data storage $DM_1$.

Figure 13:
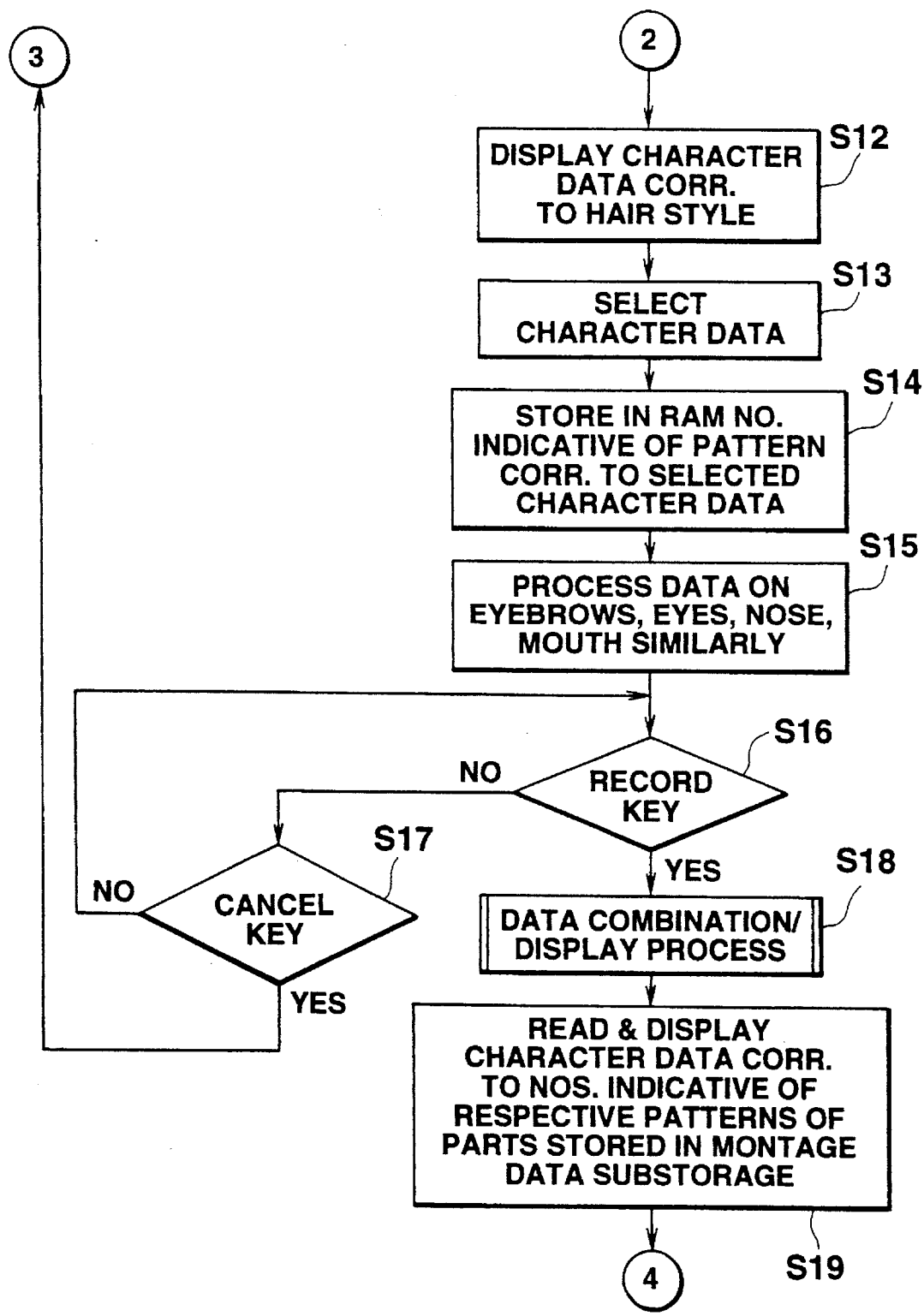
FIG. 13 is a flowchart indicative of the montage creation process continued from FIG. 12.

Control then passes to step S12 of FIG. 13, where a list of "character" data corresponding to the "hair style" of the parts of FIGS. 4 or 5 stored in the part pattern ROM 21 is displayed on the basis of a value F in the "sex discrimination" register F. Control then passes to step S13, where the upward and downward arrow keys 21a, 21b, and rightward and leftward arrow keys 22a, 22b are operated to move a cursor to target "character" data and the execute key 11 is operated to select the target "character" data as in the part "outline".

Figure 18D:
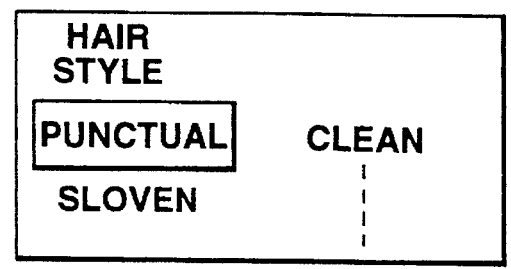

In this case, in the example, "punctual" is already selected in the default state, as shown in FIG. 18(d); and the execute key 17 is then operated to select a "punctual" character data for the "hair style" for fixing purposes.

At step S14, data on a number indicative of a pattern image in the part pattern ROM 41 corresponding to the "character" data selected for the part "hair style" is stored in the substorage PN2 which stores data on a number indicative of the pattern image of a "hair style" in the montage data substorage of the individual's data storage $DM_I$.

Thereafter, similar selection/execution processes are iterated for "eyebrows", "eyes", "nose" and "mouth" data on fixed numbers indicative of the respective pattern images of the parts is stored in the substorages PN3–PN6 of the montage data substorage of the individual's data storage $DM_I$ (step S15).

Control then passes to step S16, where it is determined whether those data items have been temporarily stored, or whether the record key 18 has been operated. If not, control passes to step S17, where it is determined whether the cancel key 19 has been operated. If not, control returns to step S16.

That is, steps S16, S17 are iterated until the record key 18 or cancel key 19 is operated.

When the respective parts are wrongly selected and the cancel key 19 is operated to cancel the data keyed in so far, this operation is determined at step S17 and the above steps S6–S15 are iterated.

When the record key 18 is operated for temporary recording, control passes to step S18, where a data combination/display process is executed which includes reading pattern data in the part pattern ROM 41 corresponding to data on the numbers indicative of the respective pattern images of the parts stored in the montage data substorage of the individual data storage $DM_I$, combining the read pattern data in the synthesis RAM 43 and displaying the resulting synthesized montage. The data combination/display process will be described in FIG. 17 in more detail later.

Control then passes to step S19, where "character data corresponding to data on the numbers indicative of the parts stored in the storages PN1–PN6 of the montage data substorage is read from the part pattern ROM 41 and displayed.

Figure 18E:
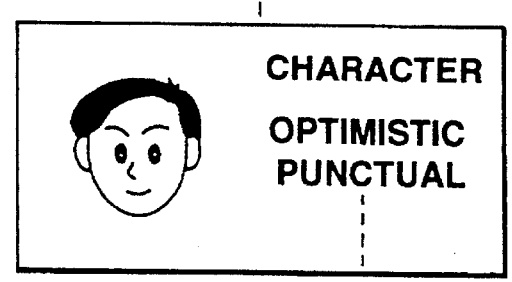

FIG. 18(e) shows a montage image and the "character" data for each of the read parts displayed on the display 3 on the basis of steps S18 and S19.

Figure 14:
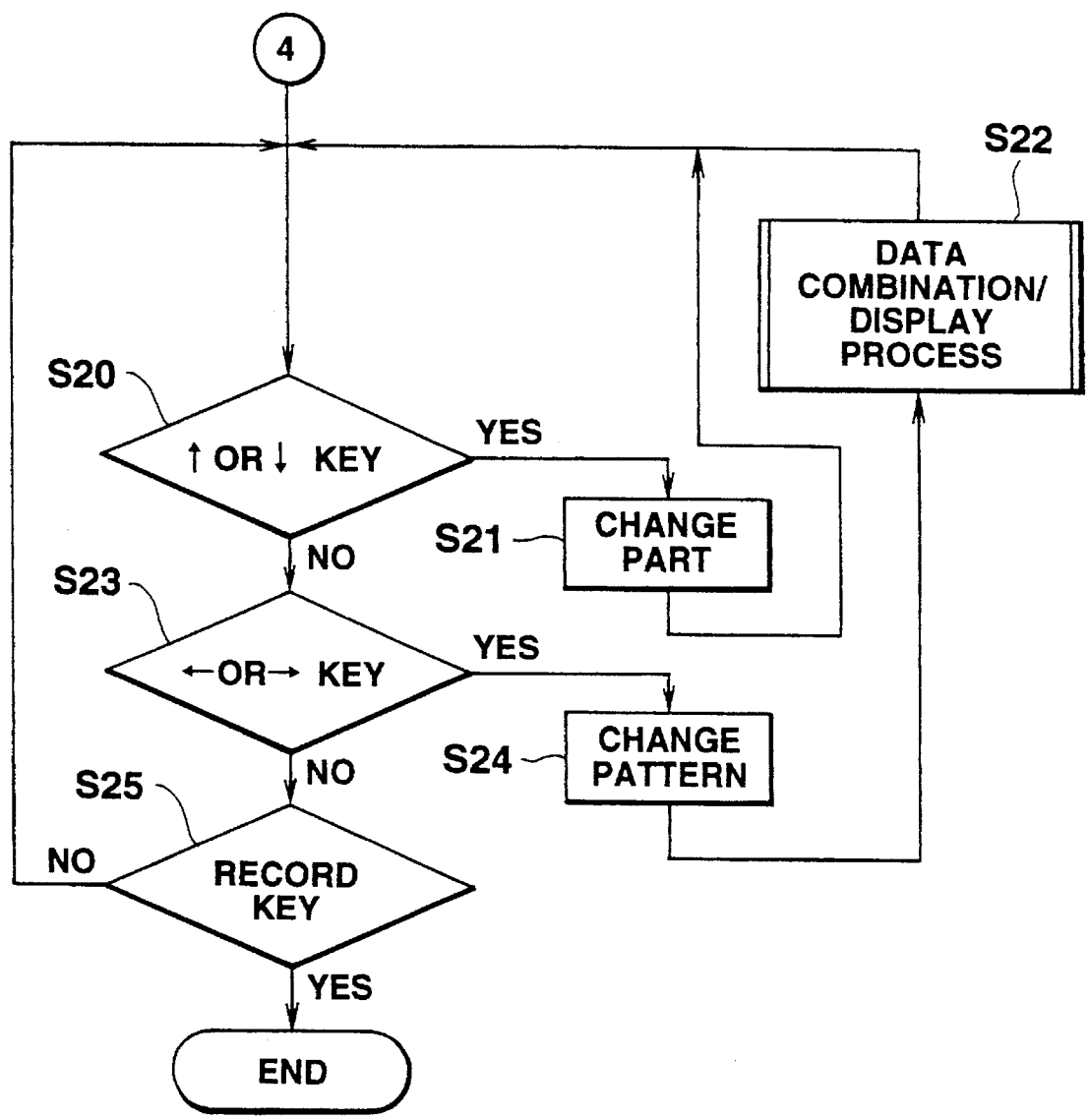
FIG. 14 is a flowchart indicative of the montage creation process continued from FIG. 13.

A part pattern changing process for the montage image recorded temporarily starts (FIG. 14). First, at step S20 it is determined whether either the upward or downward arrow key 21a or 21b has been operated which is used to select a part to be changed. The downward arrow key 21b selectively designates the parts "outline", "hair style", "eyebrows", "eyes", "nose", and "mouth" of the montage image in this order while the upward arrow key 21a selectively designates the parts "outline", "hair style", "eyebrows", "eyes", "nose", and "mouth" of the montage in an order reverse to that in the downward arrow key 21b.

If so at step S20, control passes to step S21, where the next or last part in its order of arrangement is newly selectively and designated.

If not at step S20, control passes to step S23, where it is determined whether either the rightward or leftward arrow key 22a or 22b has been operated.

The keys 22a, 22b are used to change the respective pattern images of the parts. The key 22a changes the pattern image stored in the montage data substorage to a pattern image indicated by the next number while the key 22b changes the pattern image stored in the montage data substorage to a pattern image indicated by the last number.

When the key 22a or 22b is operated, control passes to step S24, where the pattern image of the selected part is changed; that is, the number indicative of the pattern image of the selected part in the number data substorage is incremented or decremented by one.

Thereafter, control passes to step S22, where the data combination/display process is performed on the basis of the changed part, as follows (the flowchart of FIG. 17).

In this process, first, at step Q1 data on a number indicative of the pattern image of the "outline" is read as data on the "outline" from the "outline" substorage PN1 of the montage data substorage of the individual's data storage $DM_I$. At step Q2 data on the pattern of the "outline" corresponding to data on the number is read from the part pattern ROM 41 and transferred to and stored in the synthesis RAM 43.

Next, at step Q3 data on a number is read as data on the "hair style" from the "outline" substorage PN2. At step Q4 data on the pattern of the "hair style" for data on the number is read from the ROM 41 and transferred to and stored in the synthesis RAM 43.

Subsequently, data on the "eyebrows", "eyes", "nose", and "mouth" is processed in a manner similar to that in the process for the data on the "outline" and "hair style" and predetermined pattern data is transferred to and stored in the synthesis RAM 43 (step Q5) and all the data items in the synthesis RAM 43 are combined into a montage, which is then displayed on the display unit 3 (step Q6).

Each time the pattern is changed, data items on the changed patterns are combined and the whole resulting image is displayed, so that a montage image is created while visually confirming the pattern image.

The once or wrongly selected patterns can easily be re-selected individually, for example, in the creation of a montage.

When the changing process at steps S20–S24 is terminated, the record key 18 is operated, which is determined at step S25 to thereby terminate the montage creation process.

Figure 15:
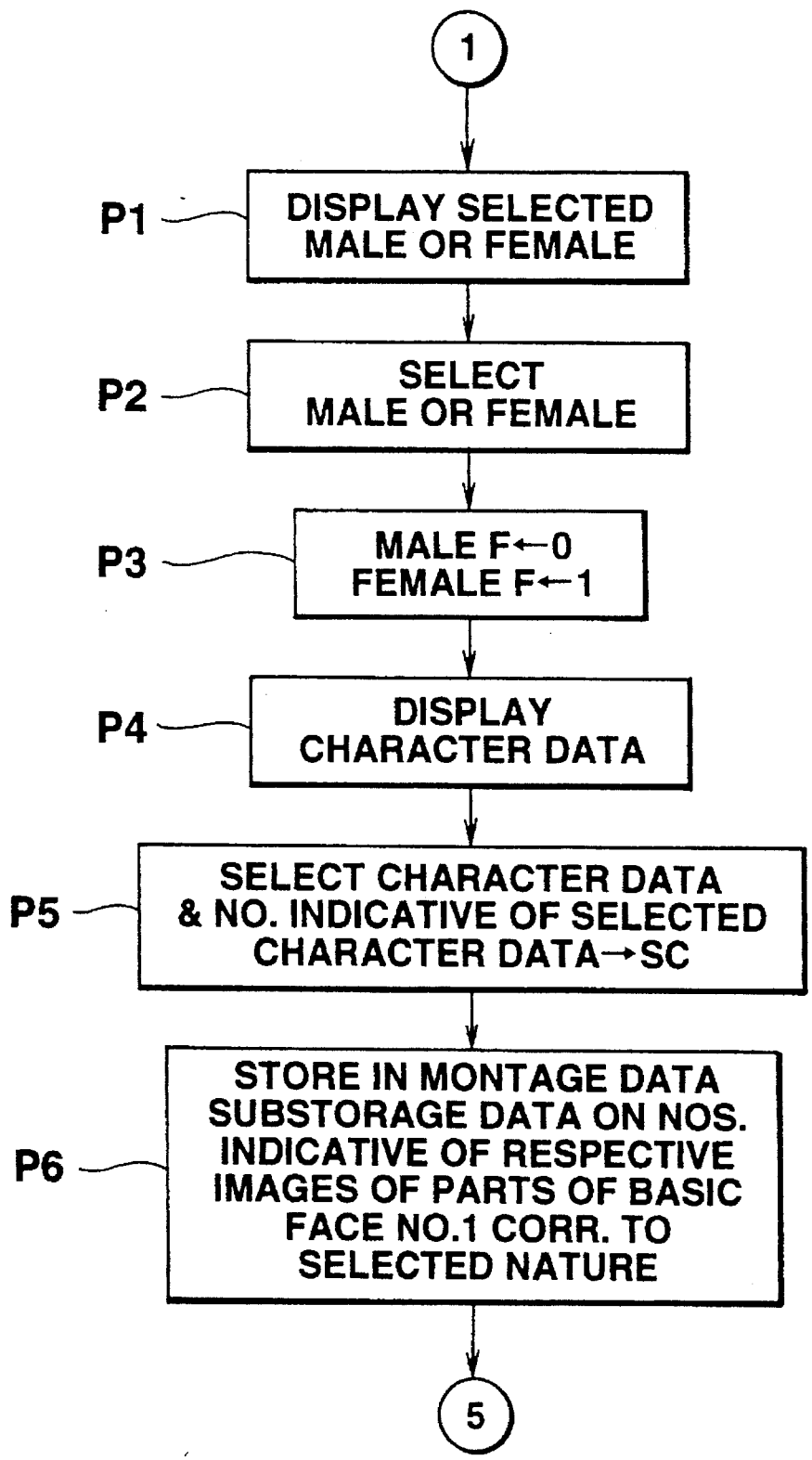
FIG. 15 is a flowchart indicative of the montage creation process continued from FIG. 12.

If the value of the mode register M is not "0" at step S5 or it is determined that the basic face changing mode has been selected, a basic face changing mode process starts which includes a step P1 and subsequent steps of FIG. 15.

Figure 19A:
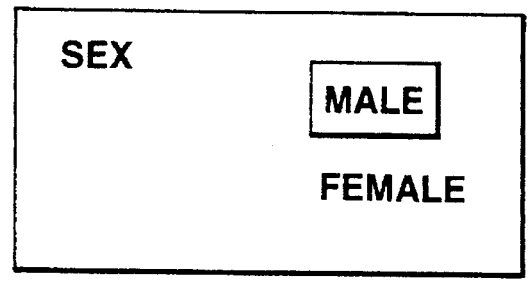
FIGS. 19(a)–19(d) illustrate a basic face changing mode process of the montage creation process of FIG. 15.
Figure 19B:
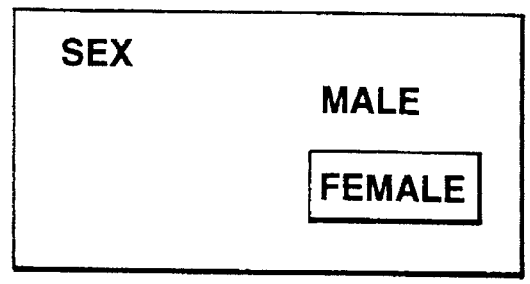

In this process, first, at step P1 a selected sex is displayed. In this case, "male" has been selected in the default state, as shown in FIG. 19(a).

At step P2 "male" or "female" is selected. In this case, since the "male" has been selected in the default state, as shown in FIG. 19(a), the execute key 17 is only required to be operated to select "male". In order to select "female", the lower selection key 20b is required to be depressed to change the selected state to "female" and the execute key 17 is then operated.

At step P3 when "male" is selected as the sex, "0" is put in the sex discrimination register F while when "female" is selected as the sex, "1" is put in the sex discrimination register F.

Thereafter, control passes to step P4, where a list of data on "character" indicated in FIGS. 6 or 7 is displayed on the basis of the data in the sex discrimination register F.

Control then starts a "character" data selection process at step P5. In this process, the upward, downward arrow keys 21a, 21b and rightward and leftward arrow keys 22a, 22b are operated to move the cursor to the target one of the displayed plurality of "character" data items and the execute key 17 is depressed to select the target "character" data.

The "character" data items have corresponding numbers. Data on a number corresponding to data on the selected "character" is set in the register SC.

Figure 19C:
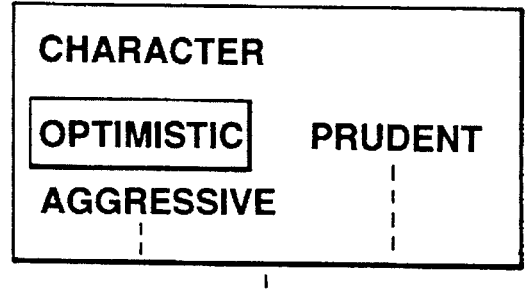
Figure 19D:
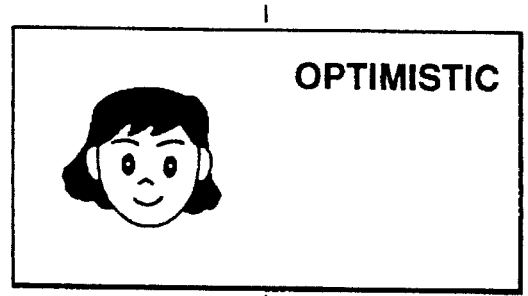

In this case, "optimistic" has been selected in the default state, as shown in FIG. 19(c). By depression of the execute key 17 under such situation, data on the character "optimistic" is selected and displayed, as shown in FIG. 19(d).

Control then passes to step P6, where data on numbers indicative of the respective pattern images of the parts of the basic face No. 1 corresponding to the selected "character" data is stored in the respective substorages PN1–PN6 of the montage data substorage.

Figure 16:
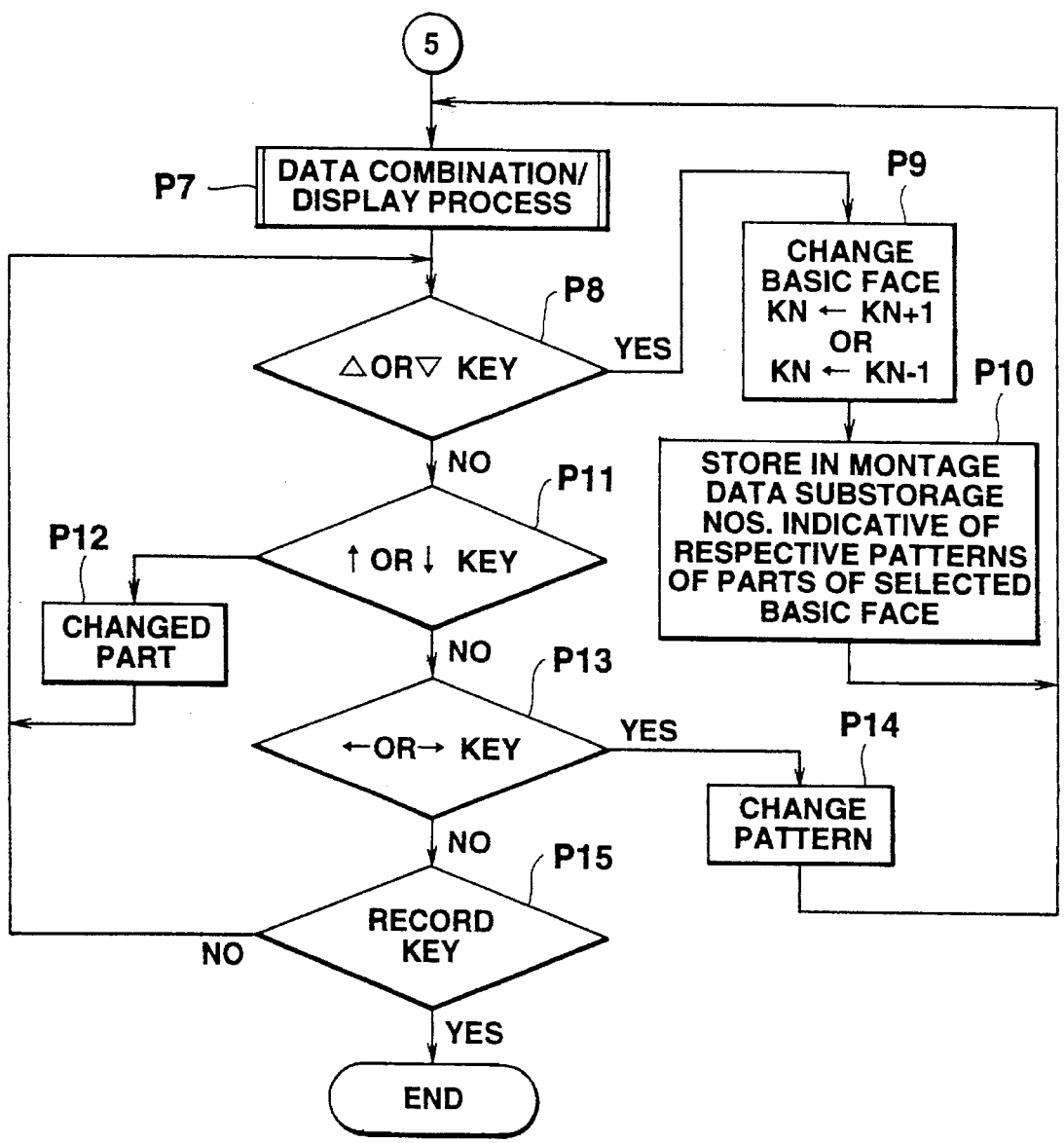
FIG. 16 is a flowchart indicative of the montage creation process continued from FIG. 15.

Control then passes to step P7 of FIG. 16, where data is combined into a montage image of a basic type No. 1 of the selected "character", which is then displayed on the display 3.

Next, the basic face and part pattern changing process at steps P8–P14 starts which includes the part pattern changing process at steps S21–S26 in the individual part selection mode and a basic face changing process.

That is, at step P8 it is determined whether the upper or lower selection key 20a or 20b has been operated. If so, control passes to step P9, where when the upper selection key 20a has been operated, the count of the basic face number storage register KN is incremented by one to change the basic face to anther basic face indicated by a number larger by one than the last one. When the lower selection key 20b has been operated, the count of the basic face number storage register KN is decremented by one to change the basic face to anther basic face indicated by a number smaller by one than the last one.

Control then passes to step P10, where data on the respective numbers indicative of the pattern images of the parts in the basic face data substorage corresponding to the basic face designated in the basic face number storage register KN of the basic face data substorage of FIGS. 6 or 7 is stored in the respective part substorages PN1–PN6 of the montage data substorage of the individual's data storage $DM_I$.

Control then passes to step P7, where a montage of the basic face of the selected "character" designated in the basic face number storage register KN is displayed.

If it is determined at step P8 the upper or lower selection key 20a or 20b has not been operated, control passes to step P11, where it is determined whether the upward or downward arrow key 21a or 21b has been operated. If so, control passes to step P12, where the next or last part in its order of arrangement is newly selectively designated as a part to be changed.

If not at step P11, control passes to step P13, where it is determined whether the arrow key 22a or 22b has been operated.

If so at step P13, control passes to step P14, where the pattern image of the part selected by the arrow key 21a or 21b is changed.

Control then passes to step P7, where the data combination/display process is performed on the basis of the changed pattern to thereby display a montage image.

When the montage image is completed in the changing process at steps P7–P15, the record key 18 is operated, which is determined at step P15 to thereby terminate the montage creation process.

While in the first embodiment all the patterns of the parts of a face are selectively designated in accordance with a "character", the pattern(s) of one or several parts on which "character" is likely to reflect may be selectively designated from among the patterns of all the parts.

Figure 20:
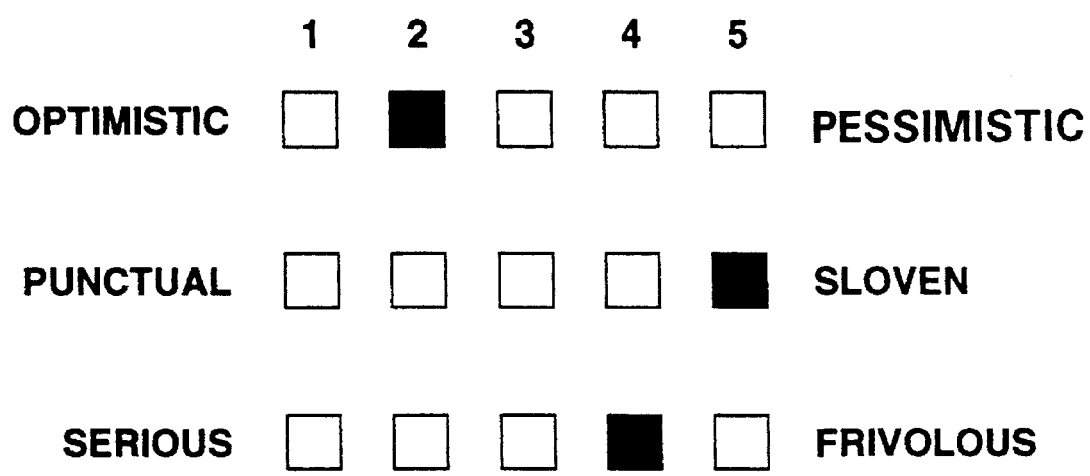
FIG. 20 shows an indicated state of a person's character when same is designated in a montage creation device of a second embodiment of the present invention.
Figure 22:
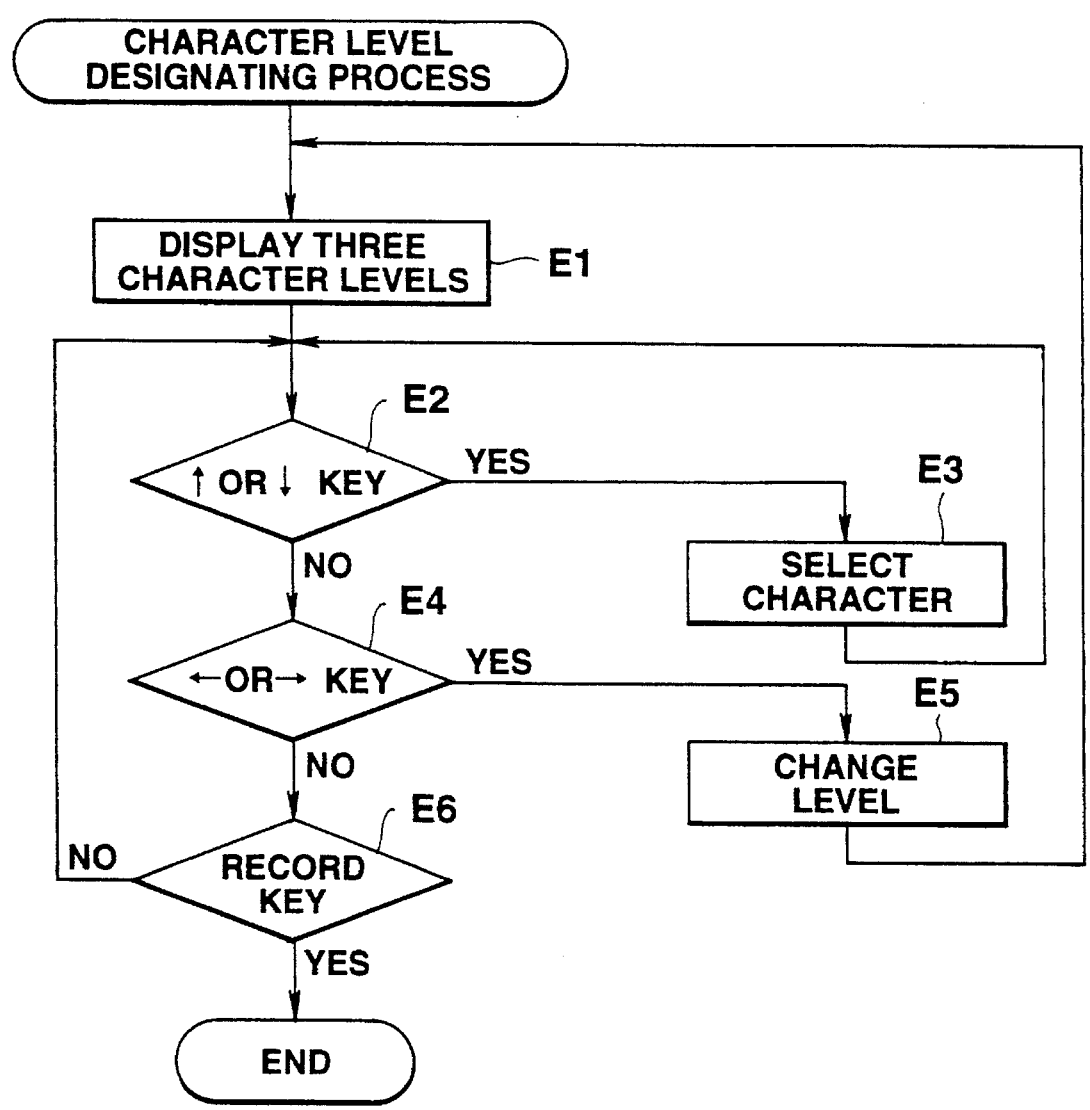
FIG. 22 is a flowchart indicative of the details of a character designating process in the montage creation device as the second embodiment.

(2) Second Embodiment:

FIGS. 20–22 show a second embodiment of the present invention. In the first embodiment, one "character" was selectively designated from among a plurality of "characters" to select the respective parts or a basic face. In the second embodiment, the respective levels of the "characters" are designated in five steps to selectively designate a respective part or a basic face on the basis of a combination of levels of the "characters".

FIG. 20 shows the displayed state of the display 3 when a level of "character" is designated. An upper display is concerned with an "optimistic" level; an intermediate display a "punctual" level; and a lower display a "serious" level.

The three "character" level displays each have a horizontal array of five display elements with words of opposite "characters" being displayed on the corresponding right and left sides of the array. For example, at the upper level, the opposite words "optimistic" and "pessimistic" are displayed.

One of the five display elements of one array is displayed in a square and the other four display elements each are displayed in a frame-like light emitter. The position of a square display element indicates which of the levels "1"–"5" it is in.

The numerals "1"–"5" indicative of the levels of the five level display elements are displayed above the corresponding five upper level display elements.

FIG. 21 shows the structure of a storage which stores data on combinations of three "character" levels, corresponding part numbers or basic face numbers. Since the three respective "characters" are settable at five levels "1"–"5", the number of combinations is 125 Thus, one of the 125 part patterns or basic faces is selectively designated.

In order to enable creation of a montage in the individual part selection mode which selects the pattern of each of the parts "outline", "hair style", "eyebrows", "eyes", "nose", and "mouth" described in detail in the first embodiment, a storage is required which stores data on combinations of three "character" levels and corresponding pattern numbers for each of those parts, as shown in FIG. 21.

In order to designate the respective levels of the three "characters", the upward and downward arrow keys 21a, 21b are operated to select one "character" whose level is desired to be designated from among the three characters "optimistic"(hereinafter referred to as character 1), "punctual" (hereinafter referred to as character 2), and "serious" (hereinafter referred to as character 3).

The rightward and leftward arrow keys 22a, 22b change the level of the selected character.

FIG. 22 shows a character level designating process. First, at step E1 the current designated levels of the three characters are displayed. Since the default values are 1 at those levels of the "character", all the three characters are displayed in square display elements of level 1 directly after the character level designating process has started.

At step E2 it is determined whether the upward or downward arrow key 21a or 21b has been operated. If so, control passes to step E3, where the character selection process is executed. In this process, each time the downward arrow key 21b is operated, the characters are selected one by one in order of character 1→character 2→character 3 while each time the upward arrow key 21a is operated, the characters are selected one by one in order of character 3→character 2→character 1.

When the process at step E3 is terminated, control returns to step E2. When it is determined at step E2 that none of the keys 21a and 21b has been operated, control passes to step E4, where it is determined whether the rightward or leftward arrow key 22a or 22b has been operated. If so, control passes to step E5, where the level changing process is executed.

At step E5 if the rightward arrow key 22a has been operated, the level of a character selected as being changed is incremented by one while if the rightward arrow key 22b is operated, the level of the character selected as being changed is decremented by one.

Thereafter, control passes to step E1, where the changed level is displayed.

When the three character levels are designated as described above, the record key 18 is operated, which is determined at step E6 to thereby terminate the character designating process.

In a method in which when a respective one of the part patterns or basic faces is selectively designated by designating a plurality of character levels as in the second embodiment, one part pattern or one basic face is easily selectively designated from among many part patterns or basic faces.

While in the respective embodiments data on patterns corresponding to characters is beforehand stored in the part pattern ROM, the face of a person associated with one character varies depending on the user. Thus, if data on a pattern image corresponding to a character is stored beforehand along with a character in corresponding manner on the basis of the user's image in a RAM which constitutes a memory which stores pattern data used for creation of pattern images, a montage of a person imaged from the character is easily created.

While in the above embodiments a person's face is described as an example of a montage image displayed, montage images to be displayed are not limited to the examples. For example, other faces of other animals such as dogs or cats may be used as montage images.

What is claimed is:

1. An electronic montage image creation device for creating a montage image of a person, the apparatus comprising:

pattern storage means for storing a plurality of patterns of each of a plurality of parts which constitute a human face;

character designating means for designating a personality character such as any of prudent, optimistic, pessimistic, punctual, clean, sloven, aggressive, speculative, passive, serious, frivolous, capricious, and the like, of the person whose montage image is to be created;

pattern designating means for selectively designating a pattern of each of the plurality of parts from among the patterns of the parts stored in said pattern storage means, on the basis of the personality character designated by said character designating means; and combining means for combining the respective patterns of the parts designated by the pattern designating means to create a montage image of the person having the designated personality character, and for displaying the created montage image of the person.

2. An electronic montage creation device according to claim 1, wherein:

said character designating means comprises individual-part character designating means for designating a personality character for each of the plurality of parts; and said pattern designating means selectively designates a pattern of each of the plurality of parts from among the patterns of the parts stored in said pattern storage means on the basis of the personality character of that part designated by said individual-part character designating means.

3. An electronic montage image creation device according to claim 1, wherein each pattern is stored in said pattern storage means in correspondence to a personality character to be designated by said character designating means.

4. An electronic montage image creation device according to claim 1, further comprising replacing means for replacing the pattern of one of the parts which is included in the montage image displayed by said combining means with another pattern of said part stored in said pattern storage means.

5. An electronic montage image creation device according to claim 1, further comprising:

part selecting means for selecting one of the plurality of parts; and pattern changing means for replacing the pattern of the part selected by said part selecting means with another pattern of the selected part stored in said pattern storage means.

6. An electronic montage image creation device according to claim 1, further comprising:

personal data designating means for designating personal data different from the personality character designated by said character designating means; and wherein:

said pattern designating means selectively designates a pattern of the part on the basis of the personality character designated by said character designating means and the personal data designated by said personal data designating means.

7. An electronic montage image creation device for creating a montage image of a person, the apparatus comprising:

pattern storage means for storing a plurality of patterns of each of a plurality of parts which constitute a human face;

basic face data storage means for storing a plurality of data items, each data item designating patterns of the respective parts, respective combinations of which patterns represent respective basic human face images, the data items being stored in correspondence with a respective basic human face image;

character designating means for designating a personality character such as any of prudent, optimistic, pessimistic, punctual, clean, sloven, aggressive, speculative, passive, serious, frivolous, capricious, and the like, of the person whose face image is to be created;

basic face selecting means for selecting one of a plurality of basic human face images on the basis of the personality character designated by said character designating means;

pattern reading means for reading out patterns of the parts from said pattern storage means on the basis of data stored in said basic face data storage means, the data being stored in correspondence with the basic face image selected by said basic face selecting means; and combining means for combining the patterns of the parts read out by said pattern reading means to compose a face image of the person having the designated personality character, and for displaying the composed face image.

8. An electronic montage image creation device according to claim 7, further comprising basic face changing means for changing the displayed basic face image selected by said basic face selecting means to another basic face image.

9. An electronic montage image creation device according to claim 7, further comprising replacing means for replacing the pattern of the part included in the face image composed and displayed by said combining means with another pattern of said part stored in said pattern storage means.

10. An electronic montage image creation device according to claim 7, further comprising:

part selecting means for selecting one of the plurality of parts; and pattern changing means for replacing the pattern of the part selected by said part selecting means with another pattern of the selected part stored in said pattern storage means.

11. An electronic montage image creation device according to claim 7, further comprising:

personal data designating means for designating personal data different from the personality character designated by said character designating means; and wherein:

said basic face selecting means selects a basic face image on the basis of the personality character designated by said character designating means and the personal data designated by said personal data designating means.

12. An electronic montage image creation device for creating a montage image of a person, the apparatus comprising:

pattern storage means for storing a plurality of patterns of each of a plurality of parts which constitute a human face;

character level designating means for designating a level of a personality character of the person whose face image is to be created;

pattern designating means for selectively designating the pattern of each of the plurality of parts from among the plurality of patterns of the parts stored in said pattern storage means on the basis of the level of the personality character such as any of prudent, optimistic, pessimistic, punctual, clean, sloven, aggressive, speculative, passive, serious, frivolous, capricious, and the like, designated by said character level designating means; and combining means for combining the respective patterns of the parts designated by said pattern designating means into a face image of the person having the designated personality character, and for displaying the combined face image of the person.

13. An electronic montage image creation device according to claim 12, wherein:

said character level designating means designates a plurality of levels of personality characters; and said pattern designating means selectively designates the pattern of the part from among the plurality of patterns of the parts stored in said pattern storage means on the basis of the plurality of levels of personality characters designated by said character level designating means.

14. An electronic montage image creation device according to claim 12, further comprising level display means for displaying the personality character level designated by said character level designating means.

15. An electronic montage image creation device according to claim 12, further comprising replacing means for replacing the pattern of the part included in the face image displayed by said combining means with another pattern of said part stored in said pattern storage means.

16. An electronic montage image creation device according to claim 12, further comprising:

part selecting means for selecting one of the plurality of parts; and pattern changing means for replacing the pattern of the part selected by said part selecting means with another pattern of the selected part stored in said pattern storage means.

17. An electronic montage image creation device according to claim 12, further comprising:

personal data designating means for designating personal data different from the personality character designated by said character designating means; and wherein:

said pattern designating means selectively designates the pattern of the part on the basis of the personality character designated by said character designating means and the personal data designated by said personal data designating means.

18. An electronic montage image creation device for creating a montage image of a person, the apparatus comprising:

pattern data storage means for storing a plurality of patterns of each of a plurality of parts which constitute a human face;

basic face data storage means for storing a plurality of data items, each data item designating patterns of the respective parts, respective combinations of which patterns represent respective basic human face images, the data items being stored in correspondence with a respective basic human face image;

character level designating means for designating the level of a personality character such as any of prudent, optimistic, pessimistic, punctual, clean, sloven, aggressive, speculative, passive, serious, frivolous, capricious, and the like, of the person whose face image is to be created;

basic face selecting means for selecting one of a plurality of basic human face images on the basis of the personality level of the character designated by said character level designating means;

pattern reading means for reading out patterns of the parts from said pattern storage means on the basis of data stored in said basic face data storage means, the data being stored in correspondence with the basic face image selected by said basic face selecting means; and combining means for combining the patterns of the parts read out by said pattern reading means to compose a face image of the person having the designated personality character, and for displaying the composed face image.

19. An electronic montage image creation device according to claim 18, wherein:

said character level designating means designates a plurality of levels of personality characters; and said basic face selecting means selects one basic face image based on the plurality of levels of personality characters designated by said character level designating means.

20. An electronic montage image creation device according to claim 18, further comprising level display means for displaying the level of the personality character designated by said character level designating means.

21. An electronic montage image creation device according to claim 18, further comprising replacing means for replacing the pattern of the part included in the face image displayed by said combining means with another pattern of said part stored in said pattern storage means.

22. An electronic montage image creation device according to claim 18, further comprising:

part selecting means for selecting one of the plurality of parts; and pattern changing means for replacing the pattern of the part selected by said part selecting means with another pattern of the selected part stored in said pattern storage means.

23. An electronic montage image creation device according to claim 18, further comprising:

personal data designating means for designating personal data different from the personality character designated by said character designating means; and wherein:

said basic face selecting means selects one basic face image on the basis of the personality character designated by said character designating means and the personal data designated by said personal data designating means.

* * * * *